United States Patent [19]

Herskovic

[11] Patent Number: 5,523,578
[45] Date of Patent: Jun. 4, 1996

[54] ELECTROMAGNETIC RADIATION SHIELDING ARRANGEMENT AND METHOD FOR RADIATION THERAPY PATIENTS

[76] Inventor: Arnold Herskovic, 1825 Huntingwood La., Bloomfield Hills, Mich. 48304

[21] Appl. No.: 408,406

[22] Filed: Mar. 22, 1995

[51] Int. Cl.⁶ ..................................................... A61N 5/01
[52] U.S. Cl. ............................. 250/492.3; 378/65; 600/1
[58] Field of Search .......................... 250/492.3, 515.1; 378/65; 174/35 MS; 600/1

[56] References Cited

U.S. PATENT DOCUMENTS 1,574,884  3/1926  Hendricks ............................ 250/515.1
5,012,041  4/1991  Sims et al. ......................... 174/35 MS
5,103,504  4/1992  Dordevic ............................. 250/516.1

Primary Examiner—Jack I. Berman
Attorney, Agent, or Firm—John R. Benefiel

[57] ABSTRACT

An arrangement is disclosed for protecting a patient from pacemaker malfunction during radiation therapy by enclosing the patient in electromagnetic radiation shielding structure comprised of sections of metallic screen which are grounded.

10 Claims, 2 Drawing Sheets

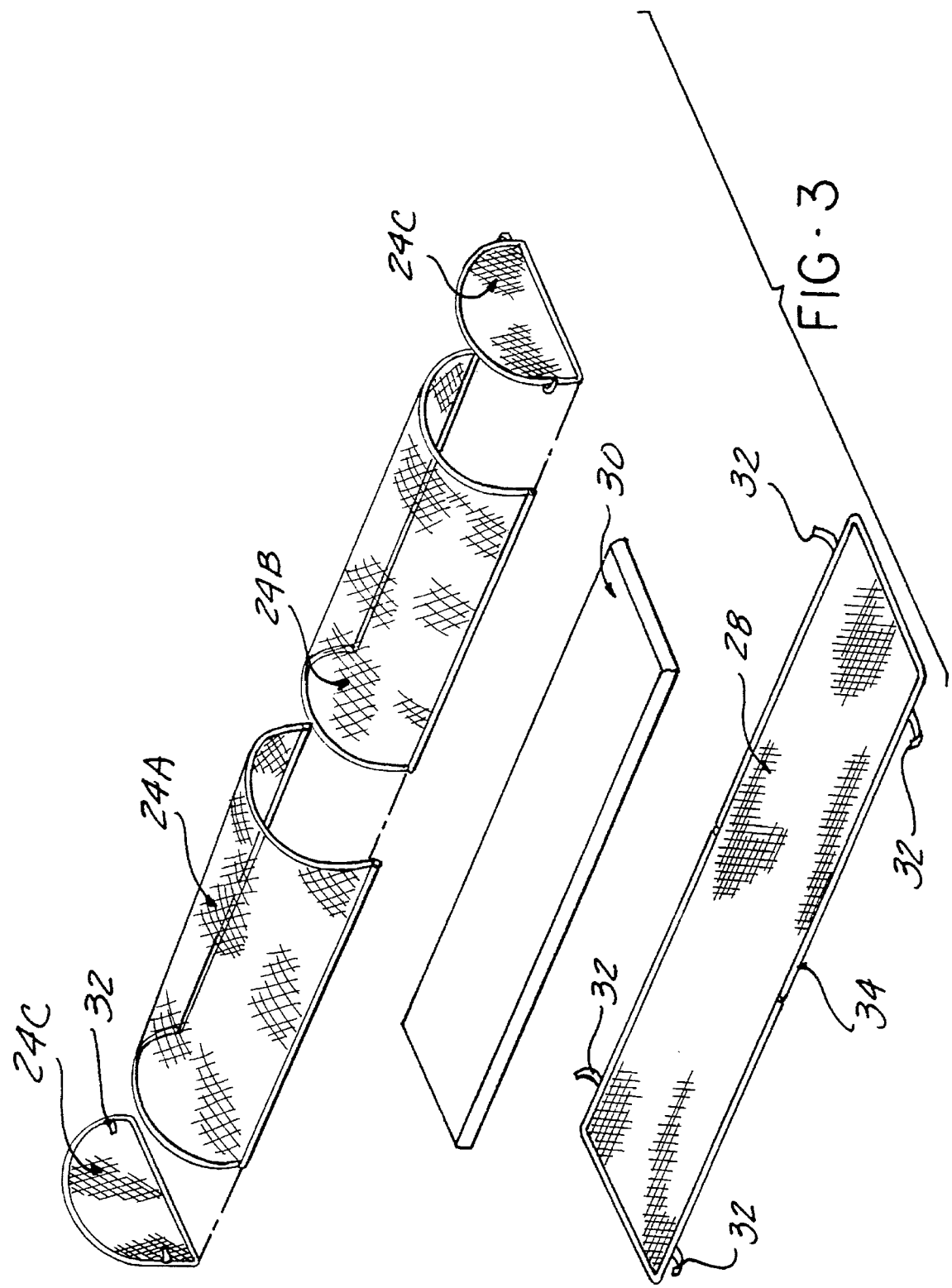

ELECTROMAGNETIC RADIATION SHIELDING ARRANGEMENT AND METHOD FOR RADIATION THERAPY PATIENTS

BACKGROUND OF THE INVENTION

Radiation therapy is increasingly used for treatment of such diseases as cancer in which tissue irradiation is used to selectively destroy certain body tissues. Radiation therapy now typically involves the use of X-ray beam generators such as linear accelerators, since naturally occurring radioactive substances suitable for this purpose more often relied on in earlier years have been replaced by more effective linear accelerators.

Linear accelerators generate electromagnetic radiation as an incidental byproduct of operation of the various electrical components incorporated therein. Electromagnetic fields have been known to create problems in the functioning of heart pacemakers, so that some risk is presented to patients having implanted pacemakers when undergoing radiation treatment with the use of linear accelerators. Shielded pacemakers have been designed for protection against malfunction during MRI imaging, but this approach increases the cost of the pacemaker and does not solve the problem for existing pacemakers. See U.S. Pat. No. 5,217,010 issued on Jun. 8, 1993 for an "EKG Amplifier and Cardiac Pacemaker for Use During Magnetic Resonance Imaging."

Shielding garments having interwoven metallic strands have also been devised for protection during MRI examinations, but this approach is not effective for protection during radiation therapy since the presence of metallic elements close to the patient's skin can cause injury due to beam scattering caused by the beam reflecting from the metal. See U.S. Pat. No. 5,103,504 issued on Apr. 14, 1992 for a "Textile Fabric Shielding Electromagnetic Radiation and Clothing Made Thereof."

While so-called Faraday cages have been used to isolate hyperthermia equipment and protect patients, heretofore no protection has been afforded radiation therapy patients.

Thus, a satisfactory solution to this problem has not heretofore been provided.

The object of the present invention is to provide reliable protection for patients having an implanted heart pacemaker while undergoing radiation therapy, protecting against the particular effects of electromagnetic radiation on pacemaker functioning, which is effective for existing implanted pacemakers, and which shielding does not itself cause injury to the patient's skin during radiation therapy.

SUMMARY OF THE INVENTION

The present invention comprises use of a patient shielding enclosure, which consists of sections of a metallic screening or similar electrically conductive screening material which are assembled together to totally enclose a patient while on a treatment couch. The enclosure is configured to have sufficient clearance with all areas of the patient's skin to avoid the burn effects of beam scattering due to the radiation beam passing through the conductive material forming the screening.

The panel sections may include an arched cover having end panels of metallic screening. The arched cover is latched to a rectangular bottom panel having an underlying electrically insulating pad on which the patient rests.

The patient shielding enclosure is electrically grounded so that the electromagnetic radiation is prevented from passing into the space within the enclosure as a result of shunting away the eddy currents generated by the electromagnetic radiation.

DESCRIPTION OF THE DRAWINGS

FIG. 3 is an exploded view of the shielding enclosure components.

DETAILED DESCRIPTION

In the following detailed description, certain specific terminology will be employed for the sake of clarity and a particular embodiment described in accordance with the requirements of 35 USC 112, but it is to be understood that the same is not intended to be limiting and should not be so construed inasmuch as the invention is capable of taking many forms and variations within the scope of the appended claims.

Figure 1:
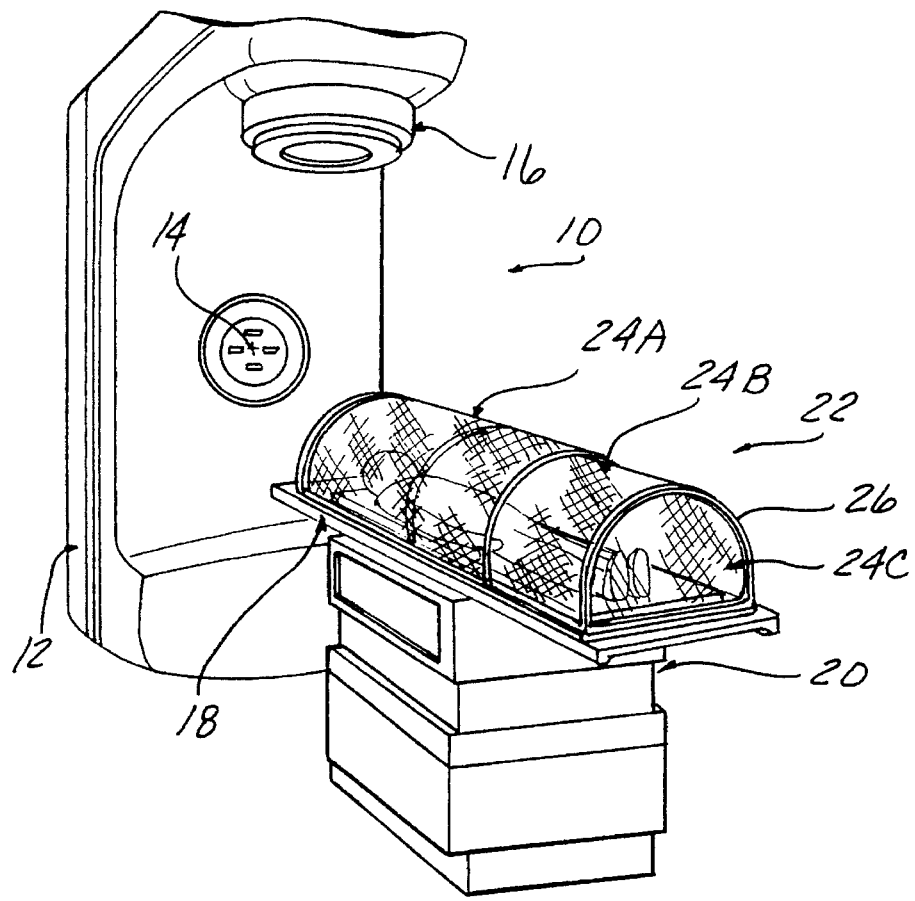
FIG. 1 is a perspective view of a linear accelerator and treatment couch having a radiation therapy patient disposed on the couch and a patient shielding enclosure according to the present invention in position surrounding the patient.

Referring to the drawings, FIG. 1 illustrates portions of a conventional linear accelerator radiation treatment unit 10, which includes a gantry 12 mounted on a stand (not shown) so as to be able to rotate about a horizontal axis 14 and enable a beam of radiation emerging from a collimator 16 to be directed at any part of a patient's anatomy with the patient lying atop a treatment couch 18. The treatment couch 18 is supported on a stand 20 for translation along each orthogonal axis in both the horizontal and vertical planes, and can position the patient overhung from the stand 20 to allow irradiation from below by rotation of the gantry to place the collimator 16 below the patient's back in an upward facing orientation. This allows irradiation of a tumor site at any location within the patient's body and from any angle so as to minimize collateral tissue injury, in the manner well known in the field.

According to the concept of the present invention, a patient shielding enclosure 22 is fitted to the treatment couch 18 which totally envelops the patient to create a shielded space occupied by the patient. The enclosure 22 is constructed of sections of an electrically conductive screen, preferably of a metal having excellent conductivity, such as copper, which sections are secured to frame members 26.

The screen sections include a top composed of arching sections 24A, 24B which extend over the patient, and maintain a clearance space on the order of 18 cm from the patient's skin, so as to prevent skin injury from scattering of the radiation beam in passing through the copper wire strands making up the screen. At the same time, a similar clearance from the collimator 16 should be maintained from all angles to minimize the deleterious effects of beam scattering, but at the same time avoiding collisions as the gantry 12 is rotated.

End sections 24c close off the ends of the arching sections 24A, 24B.

A rectangular bottom panel 28 underlies the patient, with a thick rubber spacer pad 30 placed atop the bottom panel, which is of suitable rubber material to provide electrical insulation to minimize skin injuries.

The bottom section 28, the upper sections 24A, 24B, and end sections 24C can be connected together with suitable latches 32, so as to allow convenient disassembly.

Figure 2:
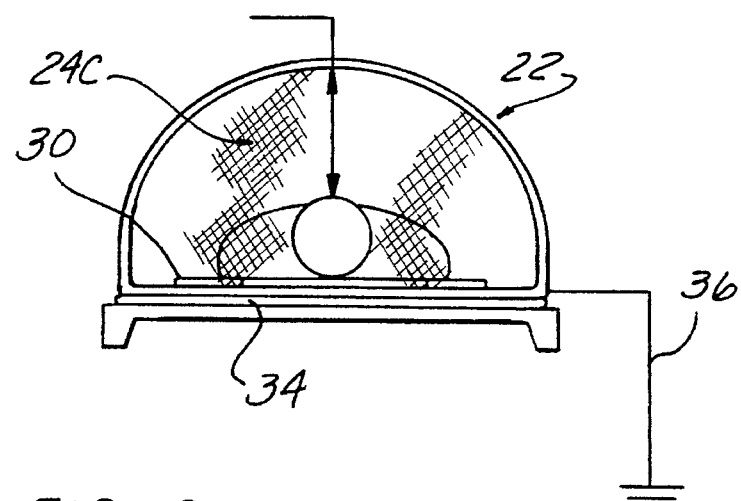
FIG. 2 is an end view of the treatment couch and patient enclosure, depicting schematically the electrical grounding.

An electrically insulating sheet 34 is interposed between the bottom section 28 and the upper surface of the treatment couch 18 to prevent eddy currents from passing into the couch 18 and stand 20. Instead, the enclosure 22 is electrically grounded by a separate grounding lead 36 shown schematically in FIG. 2.

The upper sections 24A, 24B can be separate, telescopically interfit structures to enable a size adjustment capability if desired.

Alternatively, the top sections 24A, 24B, 24C can be of integral construction to form a unitary structure sized to extend over the entire treatment couch upper surface.

Thus, a patient having an implanted pacemaker is protected by an enclosing shield from the possible effects of electromagnetic radiation or proper malfunction. It should be noted that the radiation itself can conceivably damage the pacemaker, as the present invention does not afford protection for the pacemaker from the radiation itself.

What is claimed is:

1. An arrangement for shielding a patient from electromagnetic radiation while undergoing radiation treatment in a particle accelerator apparatus and being supported on treatment couch, said arrangement comprising:

an enclosing structure disposed on said treatment couch comprised of electrically conductive screen sections defining a space within which a patient is disposed during treatment.

2. The arrangement according to claim 1 wherein said screen sections are electrically grounded so that electromagnetic radiation is prevented from passing into said space.

3. The arrangement according to claim 1 wherein said enclosing structure includes a bottom section, and wherein a spacer pad is disposed on said bottom section supporting a patient a distance above said bottom section to minimize skin injury due to scattering as radiation passes through said screen.

4. The arrangement according to claim 3 wherein said enclosure structure includes an arching top section attached to said bottom section and defining an intervening space above a patient.

5. The arrangement according to claim 4 wherein said space is on the order of 18 cm.

6. The arrangement according to claim 2 further including an electrically insulating sheet interposed between said bottom section of said screen and said treatment couch.

7. The arrangement according to claim 4 wherein said screen is formed of metal.

8. A method for protecting a patient having an implanted pacemaker during radiation therapy using a linear accelerator, the method comprising the step of enclosing the patient in an electromagnetic radiation shielding structure comprised of sections of metallic screen, the structure completely enclosing the patient from all sides.

9. The method according to claim 8 further including the step of electrically grounding the enclosure.

10. The method according to claim 8 further including the step of spacing the patient from the metallic screen sections.

* * * * *